United States Patent [19]

Tang

[11] Patent Number: 5,721,277

[45] Date of Patent: Feb. 24, 1998

[54] COMPOUNDS AND METHODS FOR INHIBITING HYPER-PROLIFERATIVE CELL GROWTH

[75] Inventor: Peng Cho Tang, Moraga, Calif.

[73] Assignee: Sugen, Inc., Redwood City, Calif.

[21] Appl. No.: 426,789

[22] Filed: Apr. 21, 1995

[51] Int. Cl.$^6$ .................... A61K 31/41; C07C 255/00
[52] U.S. Cl. .................... 514/646; 558/391; 558/392
[58] Field of Search .................... 558/391, 392; 514/646

[56] References Cited

U.S. PATENT DOCUMENTS

| | | |
|---|---|---|
| 4,087,535 | 5/1978 | Heubach et al. |
| 4,284,786 | 8/1981 | Kammerer et al. |
| 4,351,841 | 9/1982 | Kammerer et al. |
| 4,992,271 | 2/1991 | Fernandez et al. |
| 5,217,999 | 6/1993 | Levitzki et al. |
| 5,268,382 | 12/1993 | Bartlett et al. |
| 5,314,685 | 5/1994 | Tyle et al. |
| 5,476,866 | 12/1995 | Kuo et al. |
| 5,506,249 | 4/1996 | Kuo et al. |
| 5,532,259 | 7/1996 | Bartlett et al. |

FOREIGN PATENT DOCUMENTS

| | | |
|---|---|---|
| 3101093 | 1/1993 | Australia. |
| 0013376 | 12/1979 | European Pat. Off. |
| 0413329 | 2/1991 | European Pat. Off. |
| 0520722 | 6/1992 | European Pat. Off. |
| 0537742 | 10/1992 | European Pat. Off. |
| 0551230 | 7/1993 | European Pat. Off. |
| 0607775 | 7/1994 | European Pat. Off. |
| 0607776 | 7/1994 | European Pat. Off. |
| 0607777 | 7/1994 | European Pat. Off. |
| 0646578 | 9/1994 | European Pat. Off. |
| 0665013 | 1/1995 | European Pat. Off. |
| 2524959 | 12/1976 | Germany. |
| 2240104 | 7/1991 | United Kingdom. |
| 8704436 | 7/1987 | WIPO. |
| 9117748 | 11/1991 | WIPO. |
| 9221641 | 4/1992 | WIPO. |
| 9218481 | 10/1992 | WIPO. |
| 9220642 | 11/1992 | WIPO. |
| 9426260 | 11/1994 | WIPO. |
| 9521613 | 8/1995 | WIPO. |
| 9524190 | 9/1995 | WIPO. |

OTHER PUBLICATIONS

Kaur, "Tyrphostin induced growth inhibition: correlation with effect on p210$^{bcr-abl}$ autokinase activity in K562 chronic myelogenous leukemia," *Anti-Cancer Drugs* 5:213–222 (1994).

Kovalenko et al., "Selective Platelet–derived Growth Factor Receptor Kinase Blockers Reverse *sis*–Transformation," *Cancer Research* 54:6106–6114 (1994).

Mattar et al., "Effects of leflunomides active metabolite, A771726, on signal transduction pathways necessary for proliferation," *Immunobiology* 186(1–2):43 (1992) (abstract).

Borisevich et al., "Reactions of arylamides of a α–[(phenylamino)methylidene–]–β–oxo(thiono)butyric acid with hydroxylamine and substituted hydrazines," *Chemical Abstracts* 107(7):726 at abstract No. 58919a (1987).

Borisevich et al., "Reactions of arylamides of a α–[(phenylamino)methylidene]–β–oxo(thiono)butyric acid with hydroxylamine and substituted hydrazines," *Ukr. Khim. Zh.* 52(6):641–647 (1986).

Kunzek et al., "Oxydationreaktionen von α–Benzoyl–α–cyan thoacetanilid," *Zeitschrift Fur Chemi* 15(4):145–146 (1975).

Rudorf et al., "Alkylierungs–Und Arylierungsreaktionen Mit eminalen Dithiolaten," *Phosphorous and Sulfur* 9(3):329–336 (1981).

Sjogren et al., "Synthesis and Biological Activity of a Series of Diaryl–Substituted α–Cyano–β–hydroxypropenamides, a New Class of Anthelmintic Agents," *J. Med. Chem.* 34:3295–3301 (1991).

Andrews et al. (American Veterinary Medicine Association Panel on Euthanasia), "1993 Report of the AVMA Panel on Authanasia," *J. American Veterinary Medicine Association*, 202(2):229–249 (1993).

Axton et al., "Novel Immunosuppressive Butenamides," *J. Chem. Soc. Perkin Trans.* pp. 2203–2213 (1992).

Bartlett et al., "Leflunomide (HWA 486), a novel immunomodulating compound for the treatment of autoimmune disorders and reactions leading to transplantation rejection," *Agents and Actions* 32:10–21 (1991).

Bartlett et al., "Effects of lefluonomide on immune responses and models of inflammation," *Springer Semin. Immunopathol.* 14:381–394 (1993).

Bartlett et al., "Leflunomide: A novel immunomodulating drug" in *Nonsteroidal Anti–Inflammatory Drugs* 2nd ed. pp. 349–366, Lewis and Fursik eds., Dekker, NY NY (1990).

Baselga et al., "Antitumor Effects of Doxorubicin in Combination With Anti–epidermal Growth Factor Receptor Monoclonal Antibodies," *J. of Natl. Cancer Institute* 85(16):1327–1333 (1993).

Baudy et al., "Potent Quinoxaline–Spaced Phosphono α–Amino Acids of the AP-6 Type as Competitive NMDA Antagonists: Synthesis and Biological Evaluation," *J. Med. Chem.* 36:331–342 (1993).

Bilder et al., "Tyrphostins inhibit PDGF–induced DNA synthesis and associated early events in smooth muscle cells," *Am. J. Physiol.* 260(Cell Physiol.29):C721–C730 (1991).

Birchall et al., "Compositions for killing internal parasites containing 3–teri–alkyl–4–hydroxy–5–halobenzylidene–malononitriles," *Chemical Abstracts* 88:104957a (1978).

(List continued on next page.)

*Primary Examiner*—Johann Richter
*Attorney, Agent, or Firm*—Lyon & Lyon LLP

[57] ABSTRACT

The present invention features compounds and methods for inhibiting hyper-proliferative cell growth. The compounds and method are preferably used to treat patients having a hyper-proliferative cell disorder.

30 Claims, 4 Drawing Sheets

OTHER PUBLICATIONS

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bustelo and Barbacid, "Tyrosine Phosphorylation of the *vav* Proto–Incogene Product in Activated B Cells," *Science* 256:1196–1199 (1992).

Caraglia et al., "Cytosine arabinoside increases the binding of $^{125}$I–labelled epidermal growth factor and $^{125}$I–transferrin and enhances the in vitro targeting of human tumour cells with anti–(growth factor receptor)mAb," *Cancer Immunol. Immunother.* 37:150–156 (1993).

Carboni et al., "Cyanocarbon Chemistry. XI. Malononitrile Dimer," *J. Am. Chem. Soc.* 80:2838–2840 (1958).

*Cecil Textbook of Medicine,* eds. Wyngaarden, Smith, Bennett, W.B. Saunders (1992) p. 2220.

Chen and Okayama, "Calcium Phosphate–Mediated Gene Transfer: A Highly Efficient Transfection System for Stably Transforming Cells with Plasmid DNA," *BioTech.* 6:632–638 (1988).

Cherwinski et al., "The Immunosuppressant Leflunomide Inhibits Lymphocyte Progression Through Cell Cycle by a Novel Mechanism," *J. Pharmacology and Exp. Therap.* 272:460–468 (1995).

Chong et al., "Leflunomide, a Novel Immunosuppressive Agent," *Transplantation* 55:1361–1366 (1993).

Chong et al., "Leflunomide, a Novel Immunomodulatory Agent: In Vitro Analyses of the Mechanism of Immunosupression," *Transplant. Proc.* 25:747–749 (1993).

Conn et al., "Purification of a glycoprotein vascular endothelial cell mitogen from a rat glimo–derived cell line," *Proc. Natl. Acad. Sci. USA* 87:1323–1327 (1990).

Decker and Lohmann–Matthes, "A quick and simple method for the quantitation of lactate dehydrogenase release in measurements of cellular cytotoxicity and tumor necrosis factor (TNF) activity," *J. Immunol. Methods* 115:61–69 (1988).

Ehrlich and Bogert, "Experiments in the Veratrole and Quinoxaline Groups," *J. Org. Chem.* 12:522 (1947).

Ferris et al., "Synthesis of Zuinazoline Nucleosides from Ribose and Anthranilonitrile. Application of Phase–Transfer Catalysis in Nucleosides Synthesis," *J. Org. Chem.* 44(2):173–178 (1979).

Floege et al., "Factors involved in the regulation of mesangial cell proliferation *in vitro* and *in vivo*," *Kidney International* 43S:47–54 (1993).

Fry et al., "New insights into protein–tyrosine kinase receptor signaling complexes," *Protein Science* 2:1785–1797 (1993).

Gazit et al., "Tyrphostins. 1. Synthesis and Biological Activity of Protein Tyrosine Kinase Inhibitors," *J. Med. Chem.* 32:2344–2352 (1989).

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991).

Gazit et al., "Tyrphostins. 3. Structure–Activity Relationship Studies of α–Substituted Benzylidenemalononitrile 5–S–Aryltyrphostins" *J. Med. Chem.* 36:3556–3564 (1993).

Glant et al., "Immunodulation of proteoglycan–induced progressive polyarthritis by leflunomide," *Immunopharmacology* 23:105–116 (1992).

Gottardis et al., "Estradiol–Stimulated Growth of MCF–7 Tumors Implanted in Athymic Mice: A Model to Study the Tumoristatic Action of Tamoxifen," *J. Steroid Biochem.* 30(1–6):311–314 (1988).

Gulbins et al., "Tyrosine Kinase–Stimulated Guanine Nucleotide Exchange Activity of Vav in T Cell Activation," *Science* 260:822–825 (1993).

Hale et al., "Prognostic value of epidermal growth factor receptor expression in cervical carcinoma," *J. Clin. Pathol.* 46:149–153 (1993).

Hambelton and Mahon, "Drug actions on delayed–type hypersensitivity in rats with developing and established adjuvant arthritis," *Agents and Actions* 29:328–332 (1990).

Harris et al., "Breast Cancer (First of Three Parts)," *New England J. of Medicine* 327(5):319–328 (1992).

Heldin, "Structural and functional studies on platelet–derived growth factor," *EMBO Journal* 11:4251–4259 (1992).

Hoekstra et al., "Differential effects of steurosporine and tyrphostins on receptor tyrosine kinase autophosphorylation and peptide substrate phosphorylation," *Experimental Therapeutics* from 84th Annual Meeting of American Association for Cancer Research, vol. 34, #2455 (1993).

Honegger et al., "Point Mutation at the ATP Binding Site of EGF Receptor Abolishes Protein–Tyrosine Kinase Activity and Alters Cellular Routing," *Cell* 5:199–209 (1987).

Houck et al., "The Vascular Endothelial Growth Factor Family: Identification of a Fourth Molecular Species and Characterization of Alternative Splicing of RNA," *Molecular Endocrinology* 5:1806–1814 (1991).

Issidorides and Haddadin, "Benzofurazan Oxide. II. Reactions with Enolate Anions," *J. Org. Chem.* 31:4067–4068 (1966).

Ju et al., "Leflunomide inhibits cytokine–induced DNA synthesis of rabbit synovial cells in culture," *Zhongguo Yaoli Xuebao* 15:223–226 (1994).

Ju et al., "Leflunomide inhibits PAF induced DNA synthesis in rabbit synovial cells and PAF production from rat peritomeal macrophages," *Yaoxue Xuebao* 92:90–94 (1994).

Karameris et al., "Expression of Epidermal Growth Factor (EGF) and Epidermal Growth Factor Receptor (EGFR) in Gastric and Colorectal Carcinomas, An Immunohistological Study of 63 Cases," *Path. Res. Pract.* 189:133–137 (1993).

Koenders et al., "Epidermal growth factor receptor and prognosis in human breast cancer: a prospective study," *Breast Cancer Research and Treatment* 25:21–27 (1993).

Korzeniewski and Callewaert, "An Enzyme–Release Assay for Natural Cytotoxicity[1]," *J. Immunol. Methods* 64:313 (1983).

Kuechle et al., "Prevention of Kidney and Skin Graft Rejection in Rats by Leflunomide, a New Immunodulating Agent," *Transplant Proc.* 23:1083–1806 (1991).

Lee and Salemnick, "Purine N–Oxides. LXII. 2,4–Dioxopyrido[2,3–d]pyrimidine N–Oxides," *J. Org. Chem.* 40(24):3608–3610 (1975).

Levitzki, "Tyrphostins — Potential Antiproliferative Agents and Novel Molecular Tools," *Biochem. Pharm.* 40(5):913–918 (1990).

Ley and Seng, "Synthesen unter Verwendung von Benzofuroxan," *Synthesis* 197:415–422 (1975).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.*, 264:14503–14509 (1989).

Marshall, E., "Search for a Killer: Focus Shifts from Fat to Hormones," *Science* 259:618–621 (1993).

Mattar et al., "Inhibition of the epidermal growth factor receptor tyrosine kinase activity by leflunomide, " *FEBS Letters* 2:161–164 (1993).

Mattar et al., "Inhibition of the epidermal growth factor receptor tyosine kinase activity by leflunomide, " *FEBS Letters* vo;. 334:161–164 (1993) [19].

McChesney et al., "An Evaluation of Leflunomide in the Canine Renal Transplantation Model," *Transplantation* 57:1717–1722 (1994).

Millauer et al., "High Affinity VEGF Binding and Developmental Expression Suggest Flk-1 as a Major Regulator of Vasculogenesis and Angiogenesis," *Cell* 72:835–846 (1993).

Mosmann, "Rapid Colorimetric Assay for Cellular Growth and Survival: Application to Proliferation and Cytotoxicity Assays," *J. Immunol. Methods* 65:55–63 (1983).

Muller et al., "BCR First Exon Sequences Specifically Activate the *BCR/ABL* Tyrosine Kinase Oncogene of Philadelphia Chromosome–Positive Human Leukemias," *Mol. Cell. Biol.* 11:1785–1792 (1991).

Nichterlein et al., "Leflunomide (HWA 486) Prolongs Course of Murine Listeriosis," *Immunol. Infect. Dis.* 4:18–22 (19949) 1990.

Ogawa et al., "Therapeutic Effects of Leflunomide, a New Antirheumatic Drug, on Glomerulonephritis Induced by the Antibasement Membrane Antibody in Rats," *Clin. Immunol. Immunopath.* 61:103–118 (1991).

Ohmichi et al., "The Tyrosine Kinase Inhibitor Tyrphostin Blocks the Cellular Actions of Nerve Growth Factor," *Biochemistry* 32:4650–4658 (1993).

Ogawa et al., "Effects of leflunomide on glomerulonephritis induced by antibasement membrane antibody in rats," *Agents Actions* 31:321–328 (1990).

Osborne et al., "Effect of Estrogens and Antiestrogens on Growth of Human Breast Cancer Cells in Athymic Nude Mice," *Cancer Research* 45:584–590 (1985).

Osherov et al., "Selective Inhibition of the EGF and Neu receptors by Tyrophostins," *J. Cell Biochem.* S17A:237 (1993).

Ozzello and Sordat, "Behavior of Tumors Produced by Transplantation of Human Mammary Cell Lines in Athymic Nude Mice," *Eur. J. Cancer* 16:553–559 (1980).

Patteson et al., "3–Carboxy–5–methyl–N–[4–(trifluoromethyl)phenyl]–4–isoxazolecarboxamide, a New Prodrug for the Antiarthritic Agent 2–Cyano–3–hydroxy–N–[4–(trifluoromethyl)phenyl]–2–butenamide," *J. Med. Chem.* 35:507–510 (1992).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Pigott et al., "Expression of epidermal growth factor receptor in human gliblastoma multiforme," *Brit. J. Neurosurgery* 7:261–265 (1993).

Plate et al., "Vascular endothelial growth factor is a potential tumour angiogenesis factor in human glimoas in vivo," *Nature* 359:845–848 (1992).

Plate et al. "Up–Regulation of Vascular Endotheial Growth Factor and Its Cognate Receptors in a Rat Glimoa Model of Tumor Angiogenesis," *Cancer Research* 53:5822–5827 (1993).

Plate et al., "Platelet–Derived Growth Factor Receptor–β is Induced during Tumor Development and Upregulated during Tumor Progression in Endothelial Cells in Humaan Gliomas," *Laboratory Investigation* 4:529–534 (1992).

Pollack et al., "Response of malignant glioma cell lines to epidermal growth factor and platelet–derived growth factor in a serum–free medium," *J. Neurosurg.* 73:106–112 (1990).

Ren et al., "Identification of a Ten–Amino Acid Proline–Rich SH3 Binding Site," *Science* 259:1157–1161 (1993).

Rendu et al., "Inhibition of Platelet Activation of Tyrosine Kinase Inhibitors," *Biochem. Pharm.* 44(5):881–888 (1992).

Rosenthal et al., "Conditioned Medium from Mouse Sarcoma 180 Cells Contains Vascular Endothelial Growth Factor," *Growth Factors* 4:53–59 (1990).

Ross, "The pathogenesis of atherosclerosis: a perspective for the 1990s," *Nature* 362:801–809 (1993).

Rusch et al., "Differential Expression of the Epidermal Growth Factor Receptor and Its Lgands in Primary Non–Small Cell Lung Cancers and Adjacent Benign Lung," *Cancer Research* 53:2379–2385 (1993).

Rygaard and Povlsen, "Heterotransplantation of a Human Malignant Tumour in 'Nude' Mice," *Acta path. microbiol. scand.* 77:758–760 (1969).

Schorlemmer et al., "Prolongation of Allogeneic Transplanted Skin Grafts and Induction of Tolerance by Leflunomide, a New Immunosuppresive Isoxazol Derivative," *Transplant. Proc.* 25:763–767 (1993).

Schornagel et al., "Synthesis and Evaluation of 2,4–Diaminoquinazoline Antifolates with Activity Against Methotrexate–Resistant Human Tumor Cells," *Biochem. Pharm.* 33(20):3251–3255 (1984).

Scott et al., "p185$^{HER2}$ Signal Transduction in Breast Cancer Cells," *J. Bio. Chem.* 266(22):14300–14305 (1991).

Seibert et al., "Clonal Variation of MCF–7 Breast Cancer Cells *in Vitro* and in Athymic Nude Mice," *Cancer Research* 43:2223–2239 (1983).

Shafie and Grantham, "Role of Hormones in Growth and Regression of Human Breast Cancer Cells (MCF–7) Transplanted into Athymic Nude Mice," *J. Natl Cancer Institute* 67(1):51–56 (1981).

Shweiki et al., "Vascular endothelial growth factor induced by hypoxia may mediate hypoxia–initiated angiogenesis," *Nature* 359:843–845 (1992).

Skehan et al., "New Colorimetric Cytotoxicity Assay for Anticancer–Drug Screening," *J. Natl. Cancer Inst.* 82:1107–1112 (1990).

Talmadge and Twardzik, "Role of Cytokines in inflammation and Autoimmunity," *Agents and Actions* 35S:135–141 (1991).

Thoenes et al., "Leflunomide (HWA 486) Inhibits Experimental Autoimmune Tubulointerstitial Nephritis in Rats, "*Int. J. Immunopharmacol.* 11:921–929 (1989).

Ueno et al., "Inhibition of PDGF β Receptor Signal Transduction by Coexpression of a Truncated Receptor," *Science* 252:844–252 (1991).

Ulrichs et al., "Suppression of Natural Xenophile Antibodies With the Novel Immunomodulating Drug Leflunomide," *Transplant Proc.* 24:718–719 (1992).

Wada et al., "Anti–receptor antibodies reverse the phenotype of cells transformed by two interacting proto–oncogene encoded receptor proteins," *Oncogene* 5:489–495 (1990).

Waltenberger et al., "Different Signal Transduction Properties of KDR and Flt1, Two Receptors for Vascular Endothelial Growth Factor," *J. Biol. Chem.* 269:26988–26995 (1994).

Warri et al., "Estrogen Suppression of *erb*B2 Expression is Associated with Increased Growth Rate of ZR-75-I Human Breast Cancer Cells *In Vitro* and in Nude Mice," *Int. J. Cancer* 49:616–623 (1991).

Weithmann et al., "Effect of leflunomide on constitutive and inducible pathways of cellular eicosanoid generation," *Agents Actions* 41:164–170 (1994).

Williams et al., "Immunosuppressive Effects of Leflunomide in a Cardiac Allograft Model," *Transplantation Proc.* 25:745–746 (1993).

Williams et al., "Leflunomide in Experimental Transplantation," *Transplantation* 57:1223–1231 (1994).

Xiao et al., "Effect of Leflunomide in Control of Acute Rejection in Hamster-to-Rat Cardiac Xenografts," *Transplantation Proceedings* 26:1263–1265 1994).

Xiao et al., "Leflunomide Controls Rejection in Hamster to Rat Cardiac Xenografts," *Transplantation* 58:828–834 (1994).

Yaish et al., "Blocking of EGF-Dependent Cell Proliferaton of EGF Receptor Kinase Inhibitors," *Science* 242:933–935 (1988).

Yoneda et al., "The Antiproliferative Effects of Tyrosine Kinase Inhibitors Tyrphostins on a Human Squamous Cell Carcinoma *in Vitro* and in Nude Mice," *Cancer Research* 51:4430–4435 (1991).

Zeillinger et al., "EGF-R and Steroid Receptors in Breast Cancer: A Comparison with Tumor Grading, Tumor Size, Lymph Node Involvement, and Agen," *Clin. Biochem.* 26:221–227 (1993)Andrews et al. (American Veterinary Medicine Association Panel on Euthanasia), 1993 Report of the AVMA Panel on Euthanasia, *J. American Veterinary Medicine Association* 202(2):229–249 (1993).

Zielinski et al., "Effects of leflunomide (HWA 486) on expression of lymphocyte activation markers," *Agents Actions* 38:(Special Conference Issue) C80–C82 (1993).

COMPOUND AA10

COMPOUND AA11

COMPOUND AA12

COMPOUND AA13

COMPOUND AA14

COMPOUND AA15

COMPOUND AA16

COMPOUND AA17

COMPOUND AA18

COMPOUNDS AND METHODS FOR INHIBITING HYPER-PROLIFERATIVE CELL GROWTH

FIELD OF THE INVENTION

The present invention concerns compounds and methods for inhibiting hyper-proliferative cell growth.

BACKGROUND OF THE INVENTION

The citation of art provided in the present application is not an admission that the art is prior art to the claimed invention.

Hyper-proliferative cell growth contributes to different disorders such as autoimmune associated disorders, atherosclerosis, and cancers. The compounds leflunomide (also known as 5-methylisoxazole-4 carboxylic acid-(4-trifluromethyl)-anilide) and N-(4-trifluoro-methylphenyl)-2-cyano-3-hydroxycrotonamide have been said to be useful in inhibiting hyper-proliferative cell growth. Leflunomide acts as a prodrug for the in vivo formation of N-(4-trifluoromethylphenyl)-2-cyano-3-hydroxycrotonamide.

According to the abstracts of Kömmerer F.-J., et al., U.S. Pat. No. 4,284,786 (1981) and Kömmerer F.-J., et al., U.S. Pat. No. 4,351,841 (1982), leflunomide:

has antirheumatic, antiphlogistic, antipyretic and analgesic action, and can be used for the treatment of multiple sclerosis.

Heubach, U.S. Pat. No. 4,087,535 (1978) indicates that leflunomide has anti-inflammatory and analgetic properties.

Robertson S. M. and Lang L. S., European Patent Application 0,413,329A2 (published 1991) which is concerned with 5-methylisoxazole-4-carboxylic acids that encompass leflunomide, assert:

The present invention is directed to methods for treating ocular diseases with immune etiology through the use of 5-methyl-isoxazole-4-carboxylic acid anilides and hydroxyethlidene-cyano acetic acid anilide derivatives. In addition the compounds are useful for treating ocular manifestation associated with systemic diseases with immune etiology. The compounds exhibit immunosuppresive, anti-inflammatory, and mild anti-allergic activity and are useful for the treatment of eye diseases such as uveitis (including rheumatoid nodules), retinitis, allergy (vernal keratocon junctivitis and allergic or giant papillar conjunctivitis) and dry eye (Sjogren's syndrome). Additionally the compounds are useful for prolonging graft survival of corneal or other ocular tissue and are useful as surgical adjuncts in patients which are atopic or immune impaired.

The abstract of Barlett R. R. et al., entitled "*Isoxazole-4-Carboxamides and Hydroxyalklidene-Cyanoacetamides, Drugs Containing These Compounds and Use of Such Drugs*" PCT/EP90/01800, asserts:

Isoxazole-4-carboxamide derivatives and hydroxy-alkylidene-cyanoacetamide derivatives are suitable for the treatment of cancer diseases. These compounds can be prepared by prior art methods. Some of them are new and are suitable, in addition, for the treatment of rheumatic diseases.

Bartlett et al., U.S. Pat. No. 5,268,382 (1993), mentions the use of leflunomide and N-(4-trifluoro-methylphenyl)-2-cyano-3-hydroxycrotonamide to combat chronic graft-versus-host diseases, and in particular systemic lupus erythematosus.

Bartlett R. R. et al., *Agents and Actions* 32:10–21 (1991), indicates leflunomide was shown to be very effective in preventing and curing several auto-immune animal diseases.

Other publications concerning leflunomide include the following; Barlett et al., *Leflunomide: A novel immuno-modulating drug in: Nonsteroidal Anti-Inflammatory Drugs* (2nd ed.) pp. 349–366, Eds. Lewis and Furst, Dekker, New York, N.Y.; *Pharmaprojects*, PJB Publications Lts, Richmond, Surrey, U.K.; *Hoechst Present Future Plans, in: R & D Focus Drug News,* Oct. 3, 1994; *Hoechst Licensing and R & D update, in: R & D Focus Drug News,* Feb. 10, 1992; *Leflunomide, in: R & D Focus Drug News,* May 23, 1994; Xiao et al., *Transplantation* 58:828–834, 1994; Xiao et al., *Transplantation* 26:1263–1265, 1994; McChesney, et al., *Transplantation,* 57:1717–1722, 1994; Bartlett, et al., Springer Semin. *Immunopathol.,* 14:381–394, 1993; Nichterlein, et al., *Immunol. Infect. Dis.* 4:18–22, 1994; Williams, et al., *Transplantation,* 57:1223–1231, 1994; Weithmann, et al., entitled "*Use of Leflunomide for the Inhibition of Interleukin 1.alpha,*" EP 6077742 A2, 940727; Weithmann, et al., entitled "*Use of Leflunomide for the Inhibition of Interleukin 1.beta,*" EP 607775 A2, 940727; Weithmann, et al., entitled "*Use of Leflunomide for the Inhibition of Tumor Necrosis Factor .alpha.* (TNF-.alpha.)" EP 607776 A2, 940727; Weithmann, et al., entitled "*Use of Leflunomide for the Inhibition of Interleukin 8*", EP 607777 A2, 940727; Ju, et al., *Yaoxue Xuebao,* 92:90–94, 1994; Weithmann, et al., *Agents Actions,* 41:164–170, 1994; Ju, et al., *Zhongguo Yaoli Xuebao,* 15:223–226, 1994; Chong, et al., *Transplantation,* 55:1361–1366, 1993; Zielinski, et al., *Agents Actions,* 38: (Special Conference Issue) C80–C82, 1993; Chong, et al., *Transplant. Proc.,* 25:747–749, 1993; Williams, et al., *Transplant. Proc.,* 25:745–746, 1993; Schorlemmer, et al., *Transplant. Proc.,* 25:763–767, 1993; Glant, et al., *Immunopharmacology,* 23:105–116, 1992; Ulrichs, et al, *Transplant. Proc.,* 24:718–719, 1992; Ogawa, et al, *Clin. Immunol. Immunopathol.,* 61:103–118, 1991; Kuechle, et al., *Transplant. Proc.,* 23:1083–1086, 1991; Ogawa, et al, *Agents Actions,* 31:321–328, 1990; and Thoenes, et al., *Int. J. Immunopharmacol., pharmacol.,* 11:921–929, 1989.

These references mentioned in the background section are each hereby incorporated by reference herein into the present application.

SUMMARY OF THE INVENTION

The present invention features compounds and methods for inhibiting hyper-proliferative cell growth. The compounds and methods are preferably used to treat patients having a hyper-proliferative cell disorder. The compounds are believed to act either directly on hyper-proliferating cells and/or on cells supporting hyper-proliferative cell growth. Hyper-proliferative cell growth of one cell can be supported by a different cell through different mechanisms, for example, vascularization of a tumor provides for nutrients to feed the tumor, and secretion of growth factors from one cell can stimulate the growth of another cell.

"Hyper-proliferative cell growth" refers to excess cell proliferation. The excess cell proliferation is relative to that occurring with the same type of cell in the general population and/or the same type of cell obtained from a patient at an earlier time. Preferably, the compound has an $IC_{50}$ (amount of agent needed to achieve a 50% inhibition of cell growth) of 10 μM or less as determined by the growth assay described in the examples below.

"Hyper-proliferative cell disorders" refer to disorders where an excess cell proliferation of one or more subsets of cells in a multicellular organism occurs resulting in harm (e.g., discomfort or decreased life expectancy) to the multicellular organism. The excess cell proliferation can be determined by reference to the general population and/or by reference to a particular patient (e.g., at an earlier point in the patient's life). Hyper-proliferative cell disorders can occur in different types of animals and in humans, and produce different physical manifestations depending upon the affected cells. Hyper-proliferative cell disorders include cancers, blood vessel proliferative disorders, fibrotic disorders, and auto-immune disorders. Compound used for cancer treatment can preferably achieve a 50% inhibition in tumor growth after a twelve day treatment using the animal models described in the examples below.

Thus, a first aspect of the present invention features a compound able to inhibit hyper-proliferative cell growth having the chemical formula:

STRUCTURE I

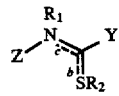

where S is sulfur;

$R_1$ is selected from the group consisting of: nothing hydrogen, alkyl, alkenyl, alkynyl, and aryl, preferably $R_1$ is hydrogen;

$R_2$ is selected from the group consisting of: aryl, alkyl, alkenyl, alkynyl and nothing, preferably $R_2$ is nothing;

Y is selected from the group consisting of: aryl, alkyl, alkenyl, and alkynyl, preferably Y is aryl or alkenyl;

Z is selected from the group consisting of: aryl, alkyl-aryl, alkenyl-aryl, and alkynyl-aryl, where the alkyl, alkenyl or alkynyl is covalently joined to the sulfur, preferably Z is aryl;

b is an optional additional bond, preferably b is present as an additional bond; and c is an optional additional bond, preferably c is not present;

provided that b or c is present as an additional bond and if b is present as the additional bond $R_2$ is nothing and c is not present as an additional bond, and if c is present as an additional bond $R_1$ is nothing and b is not present; or a pharmaceutically acceptable salt thereof.

In a preferred embodiment Structure I compounds have the chemical formula:

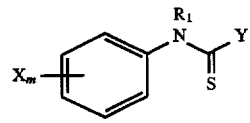

where m is 0, 1, 2, 3, 4 or 5;

each X is independently selected from the group consisting of halogen, trihalomethyl, and $NO_2$;

$R_1$ is hydrogen or lower alkyl; and

Y is either

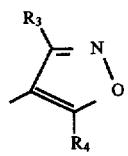

or

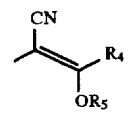

where $R_3$ is selected from the group consisting of hydrogen, carboxy, lower-alkoxy, and carbalkoxy;

$R_4$ is selected from the group consisting alkyl, alkyl-aryl, alkenyl-aryl, and alkynyl-aryl, where the alkyl is covalently joined to the heterocyclic ring; preferably $R_4$ is alkyl, more preferably $R_4$ is methyl; and $R_5$ is hydrogen or a group which is cleavable in vivo. Thus, $OR_5$ can provide the compound with a prodrug structure. Preferably, $R_5$ is selected from the group consisting of: alkyl, C(=O)-aryl, C(=O)-alkyl, C(=O)-alkenyl, C(=O)-alkynyl, hydrogen,

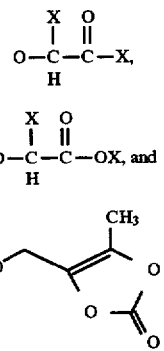

where each X is independently alkyl or hydrogen, more preferably $R_5$ is hydrogen. Further, while $OR_5$ is shown trans to CN, it should be understood that $OR_5$ may be cis to CN.

Examples of preferred Structure I compounds include AA10 (5-methyl-4-(4-trifluoromethylphenyl) aminothiocarbonylisoxazole), AA12 (1-cyano-2-hydroxy-1-(4-trifluoromethylphenylaminothiocarbonyl)propene), and AA14 (1-cyano-2-hydroxy-1-(4-trifluoromethylphenylaminothiocarbonyl)yl)propene sodium salt). AA14 which is a sodium salt of AA12, is an example of a Structure I compound formulated as a pharmaceutically acceptable salt.

A "pharmaceutical acceptable salt" is a non-toxic salt of the compound which does not prevent the compound from exerting its effect on hyper-proliferative cell growth in a patient. Preferred pharmaceutical acceptable salts include sodium, potassium, ammonium, and aluminum salts, preferably the salt is a sodium salt.

A second aspect of the present invention features a Structure II compound which can inhibit hyper-proliferative cell growth having the chemical formula:

STRUCTURE II

where S is sulfur; and

Y is selected from the group consisting of: aryl, alkyl, alkenyl, and alkynyl, preferably Y is aryl or alkenyl; and Z is selected from the group consisting of: aryl, alkyl-aryl, alkenyl-aryl, alkynyl-aryl, substituted amino-aryl, substituted amino-alkyl-aryl, preferably Z is aryl; where sulfur is covalently joined to the first substituent mentioned (e.g., in the alkyl-aryl the alkyl is covalently joined to sulfur, while in the amino-alkyl-aryl the amino is covalently joined to sulfur); or a pharmaceutically acceptable salt thereof.

In a preferred embodiment Structure II compounds have the chemical formula:

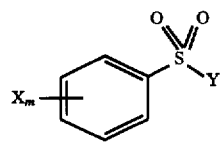

where m is 0, 1, 2, 3, 4 or 5;

each X is independently selected from the group consisting of halogen, trihalomethyl, and $NO_2$; and Y is either

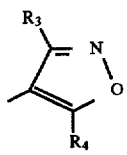

or

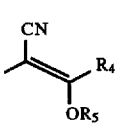

where $R_3$ is selected from the group consisting of hydrogen, carboxy, lower-alkoxy, and carbalkoxy;

$R_4$ is selected from the group consisting of alkyl, alkyl-aryl, alkenyl-aryl, and alkynyl-aryl, where the alkyl is covalently joined to the heterocyclic ring; preferably $R_4$ is alkyl, more preferably R4 is methyl; and $R_5$ is hydrogen or a group which is cleavable in vivo. Preferably, $R_5$ is selected from the group consisting of: alkyl, C(=O)-aryl, C(=O)-alkyl, C(=O)-alkenyl, C(=O)-alkynyl, hydrogen,

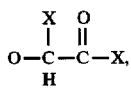

-continued

```
   X   O
   |   ||
O—C—C—OX, or
   |
   H
```

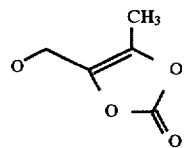

where each X is independently alkyl or hydrogen, more preferably $R_5$ is hydrogen.

Examples of preferred Structure II compounds include AA11 (4-(4-chlorophenylsulfonyl)-5-methylisoxazole), AA13 (1-(4-chlorophenylsulfonyl)-1-cyano-2-hydroxypropene), AA15 (1-(4-chlorophenylsulfonyl)-1-cyano-2-hydroxypropene sodium), AA16 (4-(4-trifluoromethylphenylaminosulfonyl)-5-methylisoxazole), AA17 (1-cyano-2-hydroxy-1-(trifluoromethylphenylaminosulfonyl)propene) and AA18 (1-cyano-2-hydroxy-1-(4-trifluoromethylphenylaminosulfonyl)propene sodium salt). AA15 which is a sodium salt of AA13, is an example of a Structure II compound formulated as a pharmaceutically acceptable salt.

Other aspects of the present invention feature methods of inhibiting hyper-proliferative cell growth using a Structure I or a Structure II compound, and methods of treating a patient having a hyper-proliferative cell disorder by administering to the patient a therapeutically effective amount of a Structure I or II compound.

Hyper-proliferative cell growth can be inhibited using a growth inhibiting amount of a Structure I or II compound (i.e., an amount sufficient to inhibit the growth of a cell exhibiting hyper-proliferative cell growth). The methods can be used to treat a patient using an ex vivo procedure where cells are removed from a patient, exposed to a sufficient amount of compound to inhibit cell growth, and then reintroduced into a patient; or in vivo.

Preferably, the compounds are used to treat a human patient suffering from a hyper-proliferative cell disorder by administering a therapeutically effective amount of the compound to the patient.

A "therapeutically effective amount," in reference to the treatment of a cancer refers to an amount sufficient to bring about one of more or the following results: reduce the size of the cancer; inhibit the metastasis of the cancer; inhibit the growth of the cancer, preferably stop cancer growth; relieve discomfort due to the cancer; and prolong the life of a patient inflicted with the cancer.

A "therapeutically effective amount," in reference to the treatment of a hyper-proliferative cell disorder other than a cancer refers to an amount sufficient to bring about one or more of the following results: inhibit the growth of cells causing the disorder, preferably stopping the cell growth; relieve discomfort due to the disorder; and prolong the life of a patient suffering from the disorder.

Structure I and II compounds can be used alone or with other agents which inhibit hyper-proliferative cell growth. For example, the compounds can be used to treat a cancer in conjunction with standard anti-cancer agents.

Thus, the present invention features two different groups of compounds (Structure I and Structure II) able to inhibit hyper-proliferative cell growth. Examples of specific compounds falling within these groups are provided along with guidelines to obtain related compounds able to inhibit hyperproliferative cell growth. For example, Structure I and Structure II compounds can be synthesized using standard synthesis techniques and the guidelines provided herein, and the ability of such compounds to inhibit a particular hyperproliferative cell disorder then can be determined using standard techniques to obtain therapeutically effective Structure I and Structure II compounds.

Other features and advantages of the invention will be apparent from the following description of the preferred embodiments thereof, and from the claims.

DETAILED DESCRIPTION OF THE INVENTION

Figure 1A:
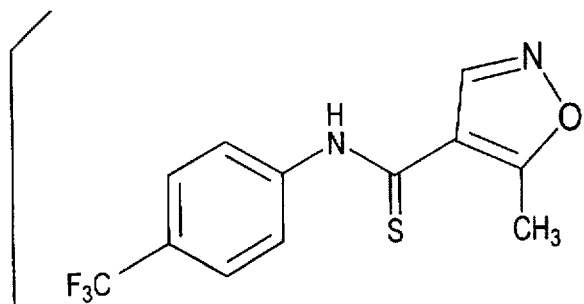
FIGS. 1a and 1b illustrate chemical structures of preferred compounds.
Figure 1A:
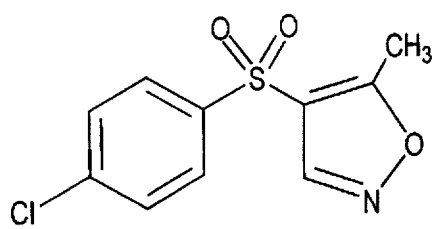
Figure 1A:
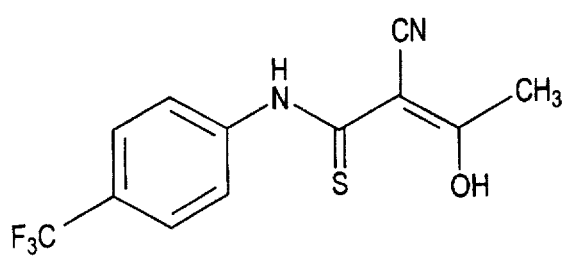
Figure 1A:
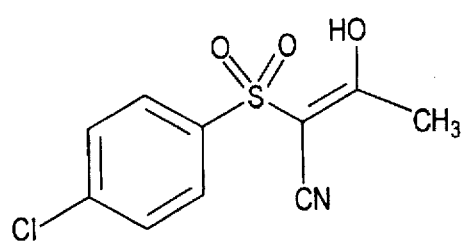
Figure 1B:
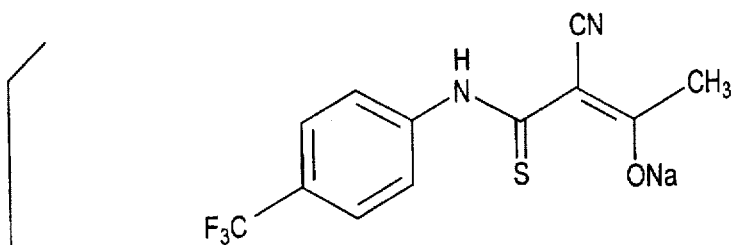
Figure 1B:
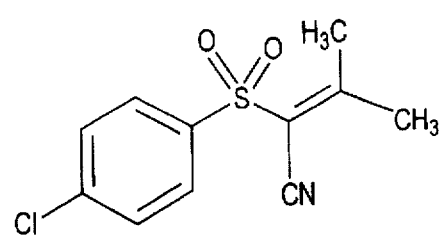
Figure 1B:
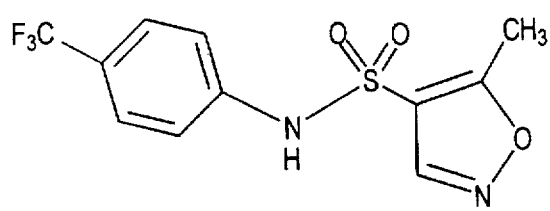
Figure 1B:
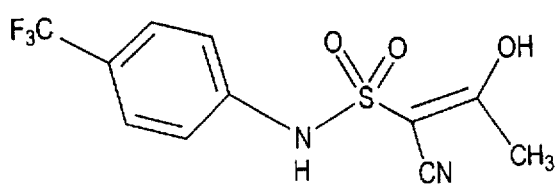
Figure 1B:
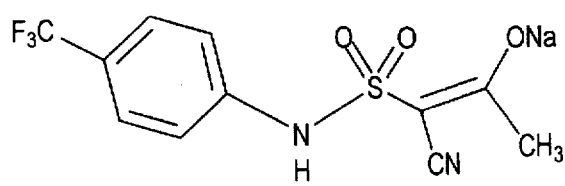

The present invention features arylaminothiocarbonyl derivative compounds and arylsulfonyl derivative compounds. The compounds can be used to treat various hyperproliferative cell disorders such as those described herein (including the Background of the Invention supra), and those described by Hirth et al., entitled "Treatment of Platelet Derived Growth Factor Related Disorders Such as Cancers" U.S. Ser. No. 08/370,574. (SUGEN Inc., the assignee of the present invention is a joint assignee of U.S. Ser. No. 08/370,574 which is hereby incorporated by reference into the present application.) Without being bound to any particularly theory, or mode of action of the compounds described herein, the compounds may be active at the platelet derived growth factor receptor (PDGF-R) and related receptor kinases such as Flt and KDR as described by U.S. Ser. No. 08/370,574. PDGF-R, Flt and KDR are discussed in more detail by Heldin, C.-H., *EMBO Journal* 11:4251–4259, 1992; Plate et al., *Laboratory Investigation* 4:529–534, 1992; Plate et al., Nature 359:845–848, 1992; Shweiki, et al., *Nature* 359:843–845, 1992; Millauer et al., *cell* 72:835–846, 1993; Plate et al., *Cancer Res.*, 53:5822–5827, 1993; and Waltenberger et al., *Journal of Biological Chemistry* 43:26988–26995, 1994 (each of these references are hereby incorporated by reference herein).

I. Chemical Definitions

The following is a list of definitions for some of the chemical groups described in the present disclosure.

An "amino" refers to —$NH_2$.

A "substituted amino" refers to $R_1$—NH—$R_2$ where $R_1$ and $R_2$ are groups which may be the same or different.

An "alkyl" refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl may be unsubstituted or may contain one or more substitutions. Multiple substitutions can be made having the same or different substituents. Preferred substitution substituents are hydroxyl, cyano, lower-alkoxy, =O, =S, $NO_2$, $N(CH_3)_2$, amino, and SH. Preferably, the alkyl has no more than three substitution substituents.

An "alkenyl" refers to an unsaturated hydrocarbon group containing at least one carbon-carbon double bond, including straight-chain, branched-chain, and cyclic groups. Preferably, the alkenyl group has 2 to 12 carbons. More preferably it is a lower alkenyl of from 2 to 7 carbons, more preferably 2 to 4 carbons. The alkenyl may be unsubstituted or may contain one or more substitutions. Multiple substitutions can be made having the same or different substituents. preferred substitution substituents are hydroxyl, cyano, lower-alkoxy, =O, =S, $NO_2$, $N(CH_3)_2$, amino, and SH. Preferably, the alkenyl has no more than three substitution substituents.

An "alkynyl" refers to an unsaturated hydrocarbon group containing at least one carbon-carbon triple bond, including straight-chain, branched-chain, and cyclic groups. Preferably, the alkynyl group has 2 to 12 carbons. More preferably, it is a lower alkynyl of from 2 to 7 carbons, more preferably 2 to 4 carbons. The alkynyl may be unsubstituted or may contain one or more substitutions. Multiple substitutions can be made having the same or different substituents. Preferred substitution substituents are hydroxyl, cyano, lower-alkoxy, =O, =S, $NO_2$, $N(CH_3)_2$, amino, and SH. Preferably, the alkynyl has no more than three substitution substituents.

By "lower" in reference to alkyl, alkenyl, alkynyl or alkoxy, is meant that 1 to 7 carbons, preferably 1 to 4 carbons, are present and the preferred substitution substituents are hydroxyl, cyano, =O, =S, $NO_2$, $N(CH_3)_2$, amino, and SH.

An "alkoxy" refers to O-alkyl, where alkyl is defined as described above.

An "aryl" refers to an aromatic group which has at least one ring having a conjugated pi electron system and includes carbocyclic aryl, heterocyclic aryl and biaryl groups, all of which may be optionally substituted. Preferred aryl substitution substituents are each independently selected from the group consisting of: halogen, trihalomethyl, hydroxyl, SH, OH, $NO_2$, amine, cyano, lower-alkoxy, lower-alkyl, lower-alkenyl, lower-alkynyl, amino, carboxy, and carbalkoxy. Preferably, the aryl contains no more than five substitution substituents.

A "carbocyclic aryl" refers to an aryl where the ring atoms on the aromatic ring are all carbon atoms. The carbon atoms are optionally substituted as described above for an aryl.

A "heterocyclic aryl" is an aryl having from 1 to 3 heteroatoms as ring atoms in the aromatic ring and the remainder of the ring atoms are carbon atoms. Suitable heteroatoms include oxygen, sulfur, and nitrogen. Examples of heterocyclic aryls include furanyl, thienyl, pyridyl, pyrrolyl, N-lower alkyl pyrrolo, pyrimidyl, pyrazinyl, imidazolyl, isoxazole, which may be substituted as described above for an aryl.

A "carbalkoxy" group refers to a COOX group, where "X" is a lower alkyl group.

II. Structure I Compounds

One group of compounds described by the present invention are arylaminothiocarbonyl derivatives described by Structure I. In a preferred embodiment, the arylaminothiocarbonyl derivative have the chemical structure:

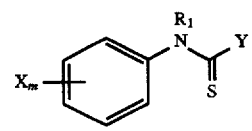

where m is 0, 1, 2, 3, 4 or 5; preferably m is 1;

each X is independently selected from the group consisting of halogen, trihalomethyl, and $NO_2$; preferably an X substituent is in the para position and each X is independently either trihalomethyl or halogen; more preferably, X is either $CF_3$ or Cl;

$R_1$ is hydrogen or lower alkyl; preferably hydrogen; and Y is either

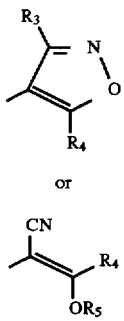

or where $R_3$ is selected from the group consisting of hydrogen, carboxy, lower-alkoxy, and carbalkoxy;

$R_4$ is selected from the group consisting alkyl, alkyl-aryl, alkenyl-aryl, and alkynyl-aryl, where the alkyl is covalently joined to the heterocyclic ring; preferably $R_4$ is alkyl, more preferably $R_4$ is methyl; and $R_5$ is hydrogen or a group which is cleavable in vivo. Preferably, $R_5$ is selected from the group consisting of: alkyl, C(=O)-aryl, C(=O)-alkyl, C(=O)-alkenyl, C(=O)-alkynyl, hydrogen,

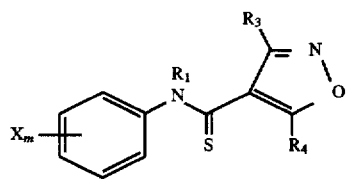

where each X is independently alkyl or hydrogen, more preferably $R_5$ is hydrogen.

In a first more preferred embodiment describing a Structure I compound, the compound has the chemical formula:

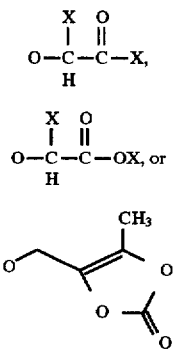

where m, X, $R_1$, $R_3$, and $R_4$ are as described for the Structure I preferred embodiment.

In a second more preferred embodiment describing a Structure I compound, the compound has the chemical formula:

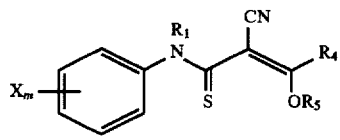

where m, X, $R_1$, $R_4$, and $R_5$ are as described for the Structure I preferred embodiment.

Structure I more preferred second embodiment compounds appear to be produced in vivo from the Structure I more preferred first embodiment compounds. For example, it is believed that AA12 is produced in vivo from AA10 by the opening of the heterocyclic ring, by the same mechanism in which N-(4-trifluoromethylphenyl)-2-cyano-3-hydroxycrotonamide is produced from leflunomide.

The $R_3$ group described in the Structure I and II compounds, when not hydrogen, is a group which is preferably cleaved in vivo. For example, Patterson et al., *J. Med. Chem.* 35:507–510 (1992) (hereby incorporated by reference herein), describe a carboxy derivative of leflunomide which, like leflunomide, can act as a prodrug for N-(4-trifluoromethylphenyl)-2-cyano-3-hydroxycrotonamide.

The solubility of compounds AA10, AA12 and AA14 are illustrated in Table I.

TABLE I

| Compound | Solubility |
|---|---|
| AA10 | ≧1,000 mg/ml in DMSO |
| AA12 | 400 mg/ml in DMSO |
| AA14 | 275 mg/ml in PBS |

PBS refers to phosphate buffered saline at pH 7.4

Compound AA14 is soluble in PBS in contrast to the anti-hyper-proliferative compounds leflunomide and N-(4-trifluoro-methylphenyl)-2-cyano-3-hydroxycrotonamide. The increased solubility of AA14 offers several advantages, for example, a larger amount of AA14 can be added at one time to achieve a longer effect thereby decreasing the need for continuous dosing, a larger amount of drug may be needed to achieve a a particular therapeutic effect, and the increase in solubility reduces the need for formulations which can have adverse side effects.

Compound AA10 in addition to differing structurally from leflunomide in also more soluble is ethanol and appears to be more stable than leflunomide. The increase in stability offer advantages, for example, a larger amount of AA10 can be added at one time to achieve a longer effect thereby decreasing the need for continuous dosing.

Also as described in the examples below, both AA10 and AA12 were able to inhibit hyper-proliferative cell growth. It could be that both AA10 and AA12 are active in inhibiting hyper-proliferative cell growth. Alternatively, the observed growth inhibition may be due primarily to AA12, and AA10 may act primarily as a prodrug.

III. Structure II Compounds

A second group of compounds described by the present invention are arylsulfonyl derivatives described by Structure II. In a preferred embodiment describing arylsulfonyl derivative the compound has the chemical structure:

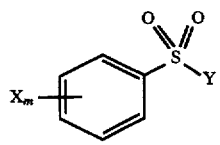

where m is 0, 1, 2, 3, 4 or 5; preferably, m is 1;

each X is independently selected from the group consisting of halogen, trihalomethyl, and $NO_2$; preferably an X substituent is in the para position and each X is independently either trihalomethyl or halogen; more preferably, X is either $CF_3$ or Cl; and Y is either

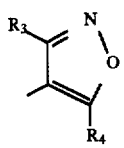

or

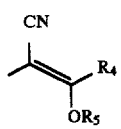

where $R_3$ is selected from the group consisting of hydrogen, carboxy, lower-alkoxy, and carbalkoxy;

$R_4$ is selected from the group consisting alkyl, alkyl-aryl aryl, alkenyl-aryl, and alkynyl-aryl, where the alkyl is covalently joined to the heterocyclic ring; preferably $R_4$ is alkyl, more preferably $R_4$ is methyl; and $R_5$ is hydrogen or a group which is cleavable in vivo. Preferably, $R_5$ is selected from the group consisting of: alkyl, C(=O)-aryl, C(=O)-alkyl, C(=O)-alkenyl, C(=O)-alkynyl, hydrogen,

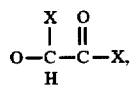

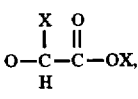

or

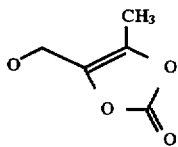

where each X is independently alkyl or hydrogen, more preferably $R_5$ is hydrogen.

A first more preferred embodiment of Structure II compounds are described by the chemical formula:

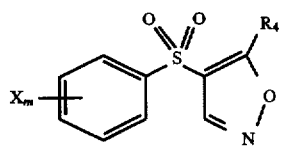

where X, m and $R_4$ are as described for the Structure II preferred embodiment.

A second more preferred embodiment of Structure II compounds are described by the chemical formula:

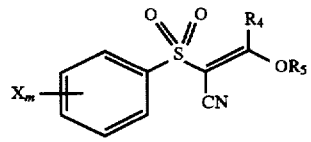

where m, X, $R_4$, and $R_5$ are as described for the Structure II preferred embodiment.

A third more preferred embodiment of Structure II compounds are described by the chemical formula:

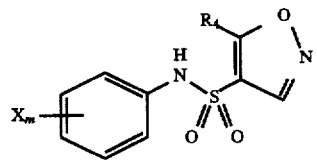

where X, m and $R_4$ are as described for the Structure II preferred embodiment.

A fourth more preferred embodiment of Structure II compounds are described by the chemical formula:

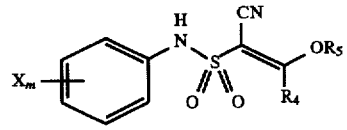

where m, X, $R_4$, and $R_5$ are as described for the Structure II preferred embodiment.

The relationship between more preferred Structure II first and second, or third and fourth, embodiment compounds is believed to be the same as the Structure I more preferred first and second embodiment compounds were the second embodiment compound are formed in vivo from the first embodiment compounds by opening of the heterocyclic ring.

IV. Hyper-Proliferative Cell Disorders

Hyper-proliferative cell disorders include cancers, blood vessel proliferation disorders, fibrotic disorders and autoimmune disorders. These disorders are not necessarily independent. For example, fibrotic disorders may be related to, or overlap with, blood vessel disorders. For example, atherosclerosis (which is characterized herein as a blood vessel disorder) results in the abnormal formation of fibrous tissue.

Blood vessel proliferation disorders refer to angiogenic and vasculogenic disorders generally resulting in abnormal proliferation of blood vessels. Examples of such disorders include restenosis, retinopathies, and atherosclerosis. The advanced lesions of atherosclerosis result from an excessive inflammatory-proliferative response to an insult to the endothelium and smooth muscle of the artery wall. (Ross R.,

*Nature* 362:801-809 (1993).) Part of the response appears to be mediated by PDGF-BB secretion, and activation of PDGF-R in endothelial and smooth muscle cells. Both cell migration and cell proliferation play a role in the formation of atherosclerotic lesions.

Fibrotic disorder are due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate PDGF-R activity can stimulate lipocyte proliferation.

Mesangial disorders are brought about by abnormal proliferation of mesangial cells. Mesangial hyper-proliferarive cell disorders include various human renal diseases, such as glomerulonephritis, diabetic nephropathy, malignant nephrosclerosis, thrombotic microangiopathy syndromes, transplant rejection, and glomerulopathies.

Cancers can be caused by abnormal growth of different types of cells. A "cancer cell" refers to various types of malignant neoplasms, most of which can invade surrounding tissues and may metastasize to different sites, as defined by Stedman's Medical Dictionary 25th edition (Hensyl ed. 1990). Examples of cancers which may be treated by the present invention include intra-axial brain cancers, ovarian cancers, colon cancers, prostate cancers, lung cancers, Kaposi's sarcoma and skin cancers.

These different types of cancers can be further characterized. For example, intra-axial brain cancers include glioblastoma multiforme, anaplastic astrocytoma, astrocytoma, ependymoma, oligodendroglioma, medulloblastoma, meningioma, sarcoma, hemangioblastoma, and pineal parenchymal.

The formation and spreading of blood vessels, or vasculogenesis and angiogenesis respectively, play important roles in a variety of physiological processes such as embryonic development, wound healing and organ regeneration. They also play a role in cancer development by facilitating vascularization of solid cancers. Thus, cancer growth can be inhibited through different mechanisms such as directly inhibiting the growth of cancer cells and/or inhibiting the growth of cells supporting cancer growth.

A. Ovarian cancer

Epithelial ovarian cancer accounts for nearly 90% of all ovarian tumors and continues to be a highly lethal malignancy. Treatment for advanced ovarian cancer generally includes cytoreductive surgery followed by combination chemotherapy with alkylating agents such as cisplatin and cyclophosphamideo. However, long term survival of advanced ovarian cancer patients is extremely poor, in the range of 10%-20%, principally because of the high incidence of metastatic tumors throughout the peritoneal cavity, and, in some cases, the lymph-nodes. Moreover, chemotherapy with cisplatin carries a potential for renal toxicity and progressive neuropathy.

Treatment of ovarian cancers can be carried out by administering a Structure I or II composition to supporting stromal cells (i.e., the framework upon which a tumor or metastatic lesion grows, including but not limited to connective tissue and vascular endothelial cells), and/or in associated vascular endothelial cells. In view of the localized spread of ovarian cancer throughout the peritoneal cavity, a preferred method of administration, particularly in advanced cases, is by intravenous or intraperitoneal injection.

B. Glioma

The compounds described herein can also be used in the treatment of primary intra-axial brain tumors of the glioma family, such as astrocytomas and glioblastomas. Glioblastoma multiforme is the most common and most malignant tumor of astrocytic origin in human adults and accounts for more than half of all primary brain tumors (See, for example, *Cecil Textbook of Medicine*, Wyngaarden, Smith, Bennett (eds) WB Saunders, 1992. p. 2220).

Gliomas have the common property of direct invasive involvement of brain tissue, are fundamentally malignant, and are inevitably fatal. Glioblastoma patients have a median survival time of less than one year even when treated aggressively with a combination of surgery, chemotherapy, and radiotherapy. Unfortunately, successful surgical intervention is extremely rare in view of the difficulty or impossibility of defining the microscopic borders of a glioma within normal brain tissue. Similarly, chemotherapy with alkylating agents has met with very little success, and no more than 10% of glioma patients respond significantly. Radiation therapy has demonstrated some value in controlling the growth of gliomas, but often results in substantial neurologic impairment. Therapy with interferon-$\beta$, in combination with radiotherapy and chemotherapy, has met with some success (DeVita, Hellman, Rosenberg (eds) *Biologic Therapy of Cancer*, J. B. Lippincott, 1991).

Intravenous and intra-arterial routes are considered to be preferred routes of administration. In addition, microcatheter technology may be particularly effective at delivering the compositions of the invention directly to the site of the glioma, thereby achieving immediate localized contact with the cancer and proximate endothelial cells and possibly minimizing potential toxicity associated with more distal intra-arterial delivery.

V. Compound Administration

A. Formulations

The compounds of the present invention can be administered to a patient alone, or in a pharmaceutical composition comprising the active compound and a carrier or excipient. The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra. PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents.

The compositions can be administered by different routes including intravenously, intraperitoneally, subcutaneously, intramuscularly, orally, topically, or transmucosally. Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, and sorbitol; cellulose preparations such as maize starch, wheat starch, rice starch, potato starch, gelatin, gum tragacanth, methyl cellulose, hydroxypropyl-methyl-cellulose, sodium carboxymethylcellulose, and polyvinylpyrrolidone (PVP). If desired, disintegrating agents may be added, such as the cross-linked polyvinyl pyrrolidone, agar, or alginic acid or a salt thereof such as sodium alginate.

Dragee cores should be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

If desired, the composition can be administered at short time intervals using a pump to control the time interval or achieve continuously administration. Suitable pumps are commercially available (e.g., the ALZET® pump sold by Alza corporation, and the BARD ambulatory PCA pump sold by Bard MedSystems).

B. Dosage

The proper dosage depends on various factors such as the type of disease being treated, the particular composition being used, and the size and physiological condition of the patient. Therapeutically effective doses can be determined using standard techniques. For example, therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors, and major organs can be also be determined to facilitate the selection of drugs most appropriate to inhibit a disorder. Such measurements can be carried out, for example, using HPLC analysis from dissected animals treated with the drug. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each study, further studies can be carried out by sacrificing the animals (preferably, in accordance with the American Veterinary Medical Association guidelines Report of the American Veterinary Medical Assoc. Panel on Euthanasia. *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a Structure I or II compound is between 1 to 2,000 mg/day, preferably 1 to 250 mg/day, and most preferably 1 to 150 mg/day. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/day. Alternatively, drugs can be administered at 0.5 to 1200 mg/m$^2$/day, preferably 0.5 to 150 mg/m$^2$/day, most preferably 0.5 to 100 mg/m$^2$/day. The average plasma level should be 50 to 5000 µg/ml, preferably 50 to 1000 µg/ml, and most preferably 10 to 500 µg/ml. Plasma levels may be reduced if pharmacological effective concentrations of the drug are achieved at the site of interest.

VI. Combination Treatment

The compounds described herein can be used alone or in combination with other types of treatment for hyperproliferative cell disorders. For example, various different types of general treatments are currently used to treat different types of cancer patients. See, Section IV supra.

VIII. EXAMPLES

Examples are provided below to illustrate different aspects and embodiments of the present invention. These examples are not intended in any way to limit the disclosed invention. Rather, they illustrate methodology by which drugs having the disclosed formula can be readily identified by routine procedure to ensure that they have the desired activity. That is, compounds within the formula claimed herein can be screened to determine those with the most appropriate activity prior to administration to an animal or human. Other compounds can also be screened to determine suitability for use in methods of this invention.

Example 1

In Vitro Tumor Inhibition

This example illustrates the ability of Structure I compounds to inhibit tumor growth using a using a growth assay. AA10, AA12 and AA14, were tested for their ability to inhibit anchorage-dependent tumor cell growth using the colorimetric assay described by Skehan, et al., *J. Natl. Cancer Inst.*, 82:1107–1112, 1990. The assay measures protein content of acid-fixed cells using the counterion binding dye sulforhodamine B (SRB, Sigma).

AA10 and AA12 were solubilized in DMSO (Sigma, cell culture grade), and AA14 was dissolved in PBS (pH 7.4), the compound were diluted into appropriate growth medium at two-fold the desired final assay concentration.

Compound (100 µL) was added to 96-well plates containing attached cellular monolayers C6 cells (2000 cells/well in 100 µL). After 4 days (37° C., 5% CO$_2$) the monolayers were washed 3 times with PBS and fixed with 200 μL ice-cold 10% trichloroacetic acid (TCA) (Fisher Scientific), and kept at 4° C. for 60 minutes. The TCA was removed and the fixed monolayers were washed 5 times with tap water and allowed to dry completely at room temperature on absorbent paper. The cellular protein was stained for 10 min with 100 μL 0.4% SRB dissolved in 1% acetic acid. After 5 washes with tap water, the dye was solubilized in 10 mM Tris base (100 μL per well) and absorbance read at 570 nm on a Dynatech plate reader model MR5000. Growth inhibition data are expressed as a percentage of absorbance detected in control wells which were treated with 0.4% DMSO or PBS alone. DMSO and PBS controls were not different from cells grown in regular growth medium. $IC_{50}$ values were determined using a four parameter curve fit function.

The results of the growth assay are shown in Table II.

TABLE II

| Compound | Growth $IC_{50}$ μM |
|---|---|
| AA10 | 2 |
| AA12 | 0.8 |
| AA14 | 0.8 |

As indicated by Table II, AA10, AA12, and AA14 all significantly (e.g., an $IC_{50}$ of less than 10 μM) inhibited tumor growth.

Example 2

In vivo Tumor Inhibition

In vivo tumor inhibition was measured using a subcutaneous Xenograft model. Mice (BALB/c, nu/nu) were implanted with C6 glioma cells and the ability of compounds AA10, AA12, and AA14 to inhibit tumor growth were measured.

C6 cells were maintained in Ham's F10 supplemented with 10% fetal bovine serum (FBS) and 2mM glutamine (GLN). Cells were harvested at or near confluence with 0.05% Trypsin-EDTA and pelleted at 450×g for 10 min. Pellets were resuspended in sterile PBS or media (without FBS) to a particular concentration and the cells were implanted into the hindflank of mice. Tumor growth was measured over 3 to 6 weeks using venier calipers. Tumor volumes were calculated as a product of length×width× height unless otherwise indicated. AA10 and AA12 were solubilized in 50-100 μL vehicle (DMSO) while AA14 was dissolved in PBS (pH 7.4). The compounds were delivered by IP injection at 15 mg/kg/day.

Figure 2:
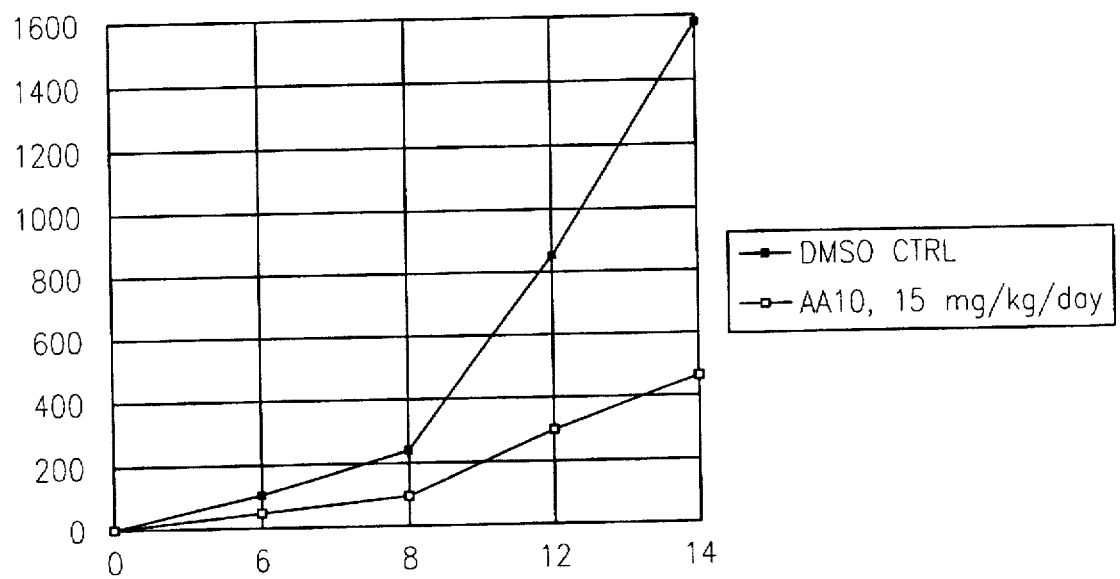
FIG. 2 illustrates the ability of AA10 to inhibit glioma cells in a Xenograft model.
Figure 3:
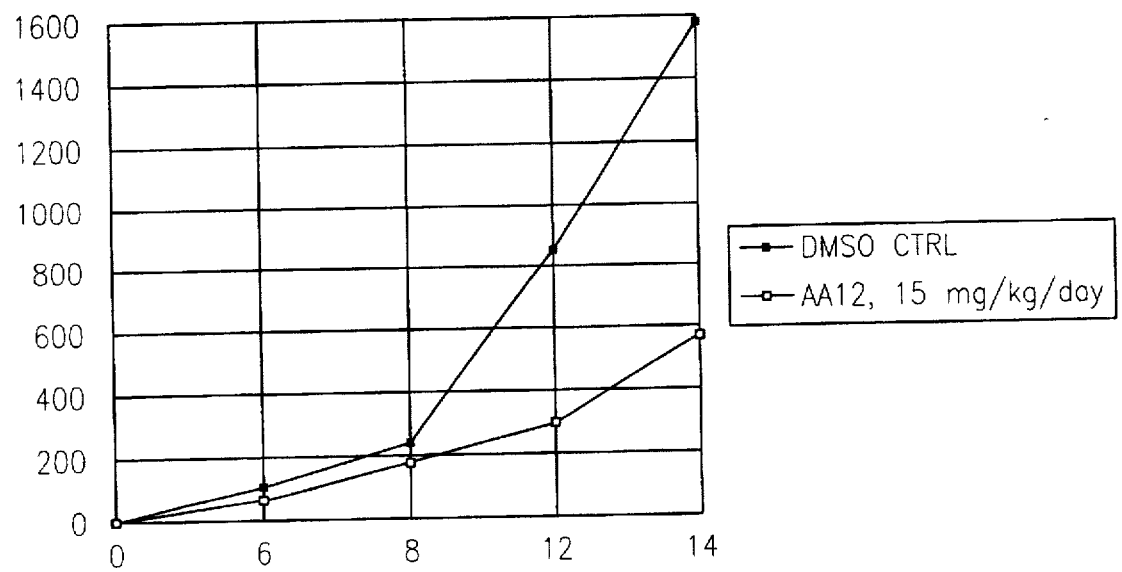
FIG. 3 illustrates the ability of AA12 to inhibit glioma cells in a Xenograft model.
Figure 4:
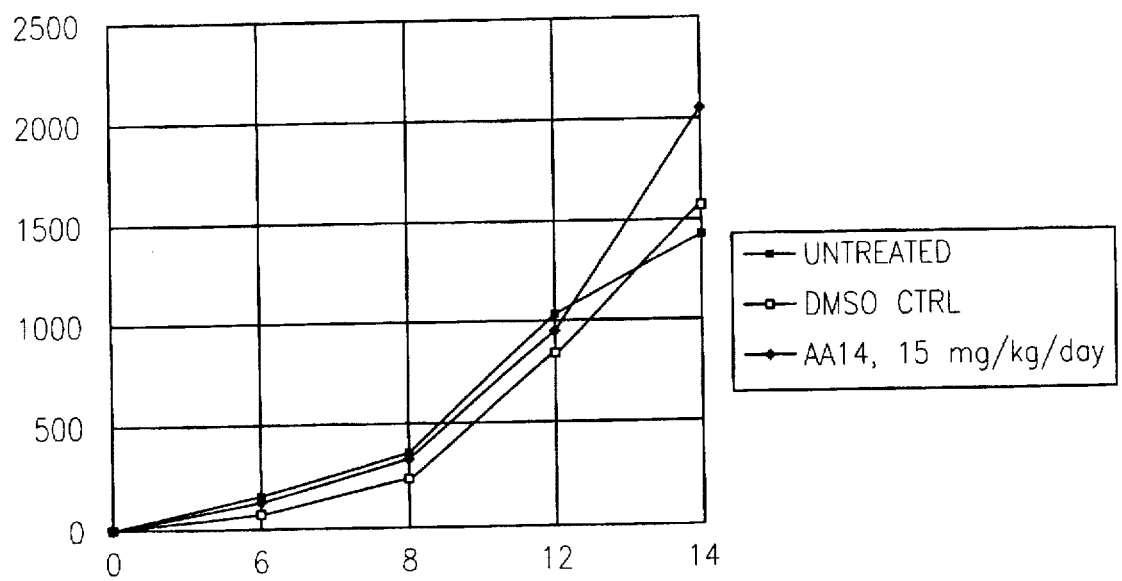
FIG. 4 illustrates the ability of AA14 to inhibit glioma cells in a Xenograft model.

FIGS. 2, 3, and 4 graphically illustrate the ability of compounds AA10, AA12, and AA14, respectively, to inhibit tumor growth. Increased efficacy can be obtained by optimizing dosing regiments. For example, the amount and timing of the doses can be varied and tested using procedures known in the art and described herein.

Example 3

Effects of Higher AA14 concentrations

Figure 5:
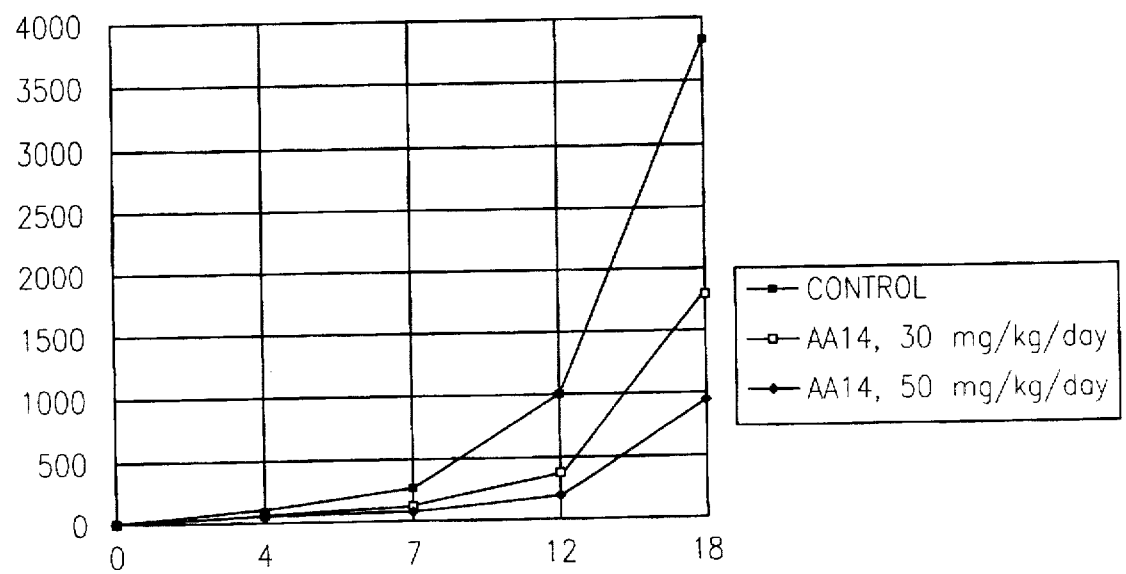
FIG. 5 illustrates the ability of higher concentrations of AA14 to inhibit glioma cells in a Xenograft model.

This example illustrates the effects of higher AA14 concentrations. The effects of higher concentrations of AA14 on mice were determined using the protocol described in Example 2. The compound was dissolved in phosphate buffered saline and the animals were treated with 30 mg/kg/day and 50 mg/kg/day. The results are shown in FIG. 5. The higher amounts of drug resulted in increased tumor inhibition.

Example 4

Toxicity Studies

Toxicity studies were carried out in animal models for AA10, AA12 and AA14. AA10 and AA12 were solubilized in DMSO and AA14 was dissolved in PBS (pH 7.4). The dosage resulting in a 50% mortality rate ($LD_{50}$) and a 10% mortality rate ($LD_{10}$) was determined as described below.

Five mice (BALB/c) were treated with different concentrations of compound. All animals were observed for 7 to 14 days after the last dose was administered. The $LD_{50}$ was calculated from a plot of % mortality versus dose (log M) using a four parameter logistic equation.

Table III illustrates the results of the different studies using different compounds.

TABLE III

| | Toxicity Studies | |
|---|---|---|
| Compound | $LD_{50}$ (mg/kg) | $LD_{10}$ (mg/kg) |
| AA10 | 96 | 77 |
| AA12 | 79 | 62 |
| AA14 | 145 | 120 |

At the end of the experiment an animal from each study administered with 100 mg/kg of compound was sacrificed and pathologically analyzed for organ damage. No significant toxicity was observed.

Example 5

Synthesis of AA10: 5-Methyl-4-(4-trifluoromethyl-phenyl) aminothiocarbonylisoxazole A solution of 24 grams of 5-methyl-4-(4-trifluoromethyl-phenyl)aminocarbonylisoxazole and 39 grams of Lawesson's reagent [2,4-bis(4-methoxyphenyl)-1,3-dithia-2,4-diphosphetane-2,4-disulfide] in 400 ml of toluene was refluxed for three hours. Upon cooling of mixture to room temperature, all the solid was filtered off and the filtrate was concentrated. The resulting crude product from the filtrate was then purified on a silica gel column with 3% methanol in dichloromethane to yield 16.5 grams of 5-methyl-4-(4-trifluoromethylphenyl)aminothiocarbonylisoxazole.

Example 6

Synthesis of AA11: 4-(4-chlorophenylsulfonyl)-5-methylisoxazole

A 10 gram suspension of 2-(4-chlorophenylsulfonyl)-1-ethoxypropene in 30 ml of ethanol was added with a solution of 1.1 equivalent of hydroxylamine in 20 ml of water. The mixture was then stirred at room temperature for 2 hours, chilled in an ice-water bath for 30 minutes and filtered. The resulting solid was crystallized in ethanol and water to provide 8.0 grams of 4-(4-chlorophenylsulfonyl)-5-methylisoxazole.

Example 7

Synthesis of AA12: 1-cyano-2-hydroxy-1-(4-trifluoromethylphenyl)aminothiocarbonylpropene A solution of 7.0 grams of 5-methyl-4-(4-trifluoromethylphenyl)aminothiocarbonylisoxazole and 5 ml of 1,8-diazabicyclo[5.4.0]undec-7-ene in 50 ml of ethanol was heated at 80° C. for 8 hours. The reaction mixture was cooled to room temperature and acidified with 6N

19 hydrochloric acid solution until pH 2. The mixture was then cooled in an ice-water bath for 30 minutes and the solid was filtered, washed with a chilled solution of ethanol and water (2:1) and dried by suction to provide 5.0 grams of 1-cyano-2-hydroxy-1-(4-trifluoromethylphenyl) aminothiocarbonylpropene.

Alternatively, AA12 can be prepared by reacting 4-trifluoromethylisothiocyanoate and 1-sodio-1-cyano acetone in tetrafuran followed by acidification.

Example 8

Synthesis of AA13: 1-(4-chlorophenylsulfonyl)-1-cyano-2-hydroxypropene

AA13 was prepared starting with AA11 using the same conditions as described for AA12.

Example 9

Synthesis of AA14: 1-cyano-2-hydroxy-1-(4-trifluoromethylphenylaminothiocarbonyl)propene sodium salt A mixture of 2.8 grams of 5-methyl-4-(4-trifluoromethylphenyl)aminothiocarbonylisoxazole and 400 mg of sodium hydroxide in 25 ml of ethanol and 10 ml of water was heated at 70° C. for 6 hours. All the ethanol was removed and the resulting solution was lyophilized to give 2 grams of 1-cyano-2-hydroxy-1-(4-trifluoromethylphenylaminothiocarbonyl)propene sodium salt.

Alternatively AA14 can be prepared by mixing AA12 with equimolar amounts of sodium hydroxide in ethanol and water followed by lyophilization.

Example 10

Synthesis of AA15: 1-(4-chlorophenylsulfonyl)-1-cyano-2-hydroxypropene sodium

AA15 was prepared from AA11 or AA13 using similar conditions as described for AA14.

Example 11

Synthesis of AA16: 4-(4-trifluoromethylphenylaminosulfonyl)-5-methylisoxazole

AA16 was prepared starting from 2-(4-trifluoromethylphenylaminosulfonyl)1-ethoxypropene under the same conditions as described for AA11.

Example 12

Synthesis of AA17: 1-cyano-2-hydroxy-1-(4-trifluoromethylphenylaminosulfonyl)propene AA17 was prepared starting from AA16 using similar conditions as described for AA12.

Alternatively, AA17 can be prepared from the sodium salt of N-3-trifluoromethylphenyl cyanomethyl sulfonamide with acetyl chloride.

Example 13

Synthesis of 18: 1-cyano-2-hydroxy-1-(4-trifluoromethylphenylaminosulfonyl)propene sodium salt AA18 was prepared from either AA16 or AA17 using similar conditions as described for AA14.

Other embodiments are within the following claims. Thus while several embodiments have been shown and described, various modifications may be made, without departing from the spirit and scope of the present invention.

20

I claim:
1. A compound having the chemical formula:

$$Z\underset{}{\overset{R_1}{\underset{}{\overset{N}{\underset{b}{\underset{SR_2}{\mid}}}}}}Y$$

or a pharmaceutically acceptable salt thereof, wherein, $R_1$ is either hydrogen, alkyl, alkenyl, alkynyl, aryl, or is not present;

$R_2$ is either aryl, alkyl, alkenyl, alkynyl, or is not present;

Y is selected from the group consisting of aryl, alkyl, alkenyl, and alkynyl;

Z is selected from the group consisting of aryl, alkyl-aryl, alkenyl-aryl, and alkynyl-aryl;

b is an optional additional bond;

c is an optional additional bond;

provided that either b or c is present as an additional bond and if b is present as the additional bond $R_2$ is not present and c is not present, and if c is present as the additional bond $R_1$ is not present and b is not present; and provided that $R_1$, $R_2$, Y, and Z are not heterocyclic.

2. The compound of claim 1, wherein $R_1$, if present, is selected from the group consisting of hydrogen, unsubstituted lower alkyl, unsubstituted lower alkenyl, unsubstituted lower alkynyl, and optionally substituted aryl optionally containing up to five substituents each independently selected from the group consisting of unsubstituted lower alkoxy, unsubstituted lower alkyl, unsubstituted lower alkenyl, unsubstituted lower alkynyl, halogen, trihalomethyl, SH, OH, $NO_2$, cyano, amino, carboxy, and unsubstituted carbalkoxy;

$R_2$, if present, is selected from the group consisting of unsubstituted lower alkyl, unsubstituted lower alkenyl, unsubstituted lower alkynyl, and optionally substituted aryl optionally containing up to five substituents each independently selected from the group consisting of unsubstituted lower alkoxy, unsubstituted lower alkyl, unsubstituted lower alkenyl, unsubstituted lower alkynyl, halogen, trihalomethyl, SH, OH, $NO_2$, cyano, amino, carboxy, and unsubstituted carbalkoxy;

Y is selected from the group consisting of:

lower alkyl optionally substituted with up to three substituents each independently selected from the group consisting of hydroxyl, cyano, unsubstituted lower alkoxy, =O, =S, $NO_2$, $N(CH_3)_2$, amino, and SH, lower alkenyl optionally substituted with up to three substituents each independently selected from the group consisting of hydroxyl, cyano, unsubstituted lower alkoxy, =O, =S, $NO_2$, $N(CH_3)_2$, amino, and SH, lower alkynyl optionally substituted with up to three substituents each independently selected from the group consisting of hydroxyl, cyano, unsubstituted lower alkoxy, =O, =S, $NO_2$, $N(CH_3)_2$, amino, and SH, and optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy;

Z is selected from the group consisting of:
optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy;

unsubstituted lower alkyl-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy;

unsubstituted lower alkenyl-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy; and unsubstituted lower alkynyl-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy.

3. The compound of claim 2, wherein $R_1$ is hydrogen;

$R_2$ is not present;

Y is lower alkenyl optionally substituted with up to three substituents each independently selected from the group consisting of hydroxyl, cyano, unsubstituted lower alkoxy, =O, =S, NO$_2$, N(CH$_3$)$_2$, amino and SH;

Z is an optionally substituted phenyl optionally containing up to five substituents each independently selected from the group consisting of halogen, trihalomethyl, SH, OH, NO$_2$, cyano, unsubstituted lower alkoxy, unsubstituted lower alkyl, unsubstituted lower alkenyl, unsubstituted lower alkynyl, amino, carboxy, and unsubstituted carbalkoxy; and b is present as an additional bond.

4. A compound having the chemical formula:

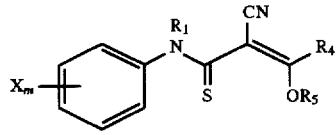

or a pharmaceutically acceptable salt thereof, wherein m is either 0, 1, 2, 3, 4 or 5;

each X is independently selected from the group consisting of halogen, trihalomethyl, and NO$_2$;

$R_1$, is hydrogen or unsubstituted lower alkyl;

$R_4$ is selected from the group consisting of unsubstituted lower alkyl, unsubstituted lower alkyl-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy, unsubstituted lower alkenyl-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy, and unsubstituted lower alkynyl-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy;

$R_5$ is selected from the group consisting of hydrogen, alkyl, C(=O)-unsubstituted lower alkyl, C(=O)-unsubstituted lower alkenyl, and C(=O)-unsubstituted lower alkynyl, and C(=O)-optionally substituted aryl optionally containing up to five substituents each independently selected from the group consisting of unsubstituted lower alkoxy, halogen, trihalomethyl, SH, OH, NO$_2$, cyano, unsubstituted lower alkyl, unsubstituted lower alkenyl, unsubstituted lower alkynyl, amino, carboxy, and unsubstituted carbalkoxy; and provided that $R_4$ and $R_5$ are not heterocyclic.

5. The compound of claim 4, wherein $R_5$ is hydrogen.

6. The compound of claim 4, wherein $R_1$ is hydrogen;

$R_4$ is methyl;

$R_5$ is hydrogen; and each X is independently selected from the group consisting of halogen and trihalomethyl.

7. A compound having the chemical formula:

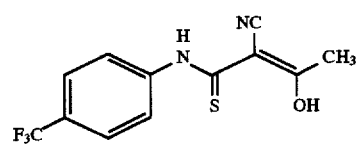

or a pharmaceutically acceptable salt thereof.

8. A pharmaceutical composition, comprising:

a pharmaceutically acceptable carrier; and a therapeutically effective amount of a compound of any one of claims 1–7.

9. A method of inhibiting growth of cells having hyperproliferative cell growth, comprising the step of exposing said cells to a growth inhibiting amount of a compound having the chemical formula:

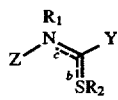

or a pharmaceutically acceptable salt thereof, wherein, $R_1$ is either hydrogen, alkyl, alkenyl, alkynyl, aryl, or is not present;

$R_2$ is either aryl, alkyl, alkenyl, alkynyl, or is not present;

Y is selected from the group consisting of aryl, alkyl, alkenyl, and alkynyl;

Z is selected from the group consisting of aryl, alkyl-aryl, alkenyl-aryl, and alkynyl-aryl;

b is an optional additional bond;

c is an optional additional bond;

provided that either b or c is present as an additional bond and if b is present as the additional bond $R_2$ is not present and c is not present, and if c is present as the additional bond $R_1$ is not present and b is not present; and provided that $R_1$, $R_2$, Y, and Z are not heterocyclic.

10. The method of claim 9, wherein $R_1$, if present, is selected from the group consisting of hydrogen, unsubstituted lower alkyl, unsubstituted lower alkenyl, unsubstituted lower alkynyl, and optionally substituted aryl optionally containing up to five substituents each independently selected from the group consisting of unsubstituted lower alkoxy, unsubstituted lower alkyl, unsubstituted lower alkenyl, unsubstituted lower alkynyl, halogen, trihalomethyl, SH, OH, $NO_2$, cyano, amino, carboxy, and unsubstituted carbalkoxy;

$R_2$, if present, is selected from the group consisting of unsubstituted lower alkyl, unsubstituted lower alkenyl, unsubstituted lower alkynyl, and optionally substituted aryl optionally containing up to five substituents each independently selected from the group consisting of unsubstituted lower alkoxy, unsubstituted lower alkyl, unsubstituted lower alkenyl, unsubstituted lower alkynyl, halogen, trihalomethyl, SH, OH, $NO_2$, cyano, amino, carboxy, and unsubstituted carbalkoxy;

Y is selected from the group consisting of:

lower alkyl optionally substituted with up to three substituents each independently selected from the group consisting of hydroxyl, cyano, unsubstituted lower alkoxy, =O, =S, $NO_2$, $N(CH_3)_2$, amino, and SH, lower alkenyl optionally substituted with up to three substituents each independently selected from the group consisting of hydroxyl, cyano, unsubstituted lower alkoxy, =O, =S, $NO_2$, $N(CH3)_2$, amino, and SH, lower alkynyl optionally substituted with up to three substituents each independently selected from the group consisting of hydroxyl, cyano, unsubstituted lower alkoxy, =O, =S, $NO_2$, $N(CH_3)2$, amino, and SH, and optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy;

Z is selected from the group consisting of:

optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy;

unsubstituted lower alkyl-optionally substituted aryl optionally containing up to five substituents each independently selected from the group consisting of unsubstituted lower alkoxy, halogen, trihalomethyl, SH, OH, NO2, cyano, unsubstituted lower alkyl, unsubstituted lower alkenyl, unsubstituted lower alkynyl, amino, carboxy, and unsubstituted carbalkoxy;

unsubstituted lower alkenyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy; and unsubstituted lower alkynyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy.

11. The method of claim 10, wherein $R_1$ is hydrogen;

$R_2$ is not present;

Y is lower alkenyl optionally substituted with up to three substituents each independently selected from the group consisting of hydroxyl, cyano, unsubstituted lower alkoxy, =O, =S, NO2, $N(CH_3)_2$, amino and SH;

Z is an optionally substituted phenyl optionally containing up to five substituents each independently selected from the group consisting of halogen, trihalomethyl, SH, OH, $NO_2$, cyano, unsubstituted lower alkoxy, unsubstituted lower alkyl, unsubstituted lower alkenyl, unsubstituted lower alkynyl, amino, carboxy, and unsubstituted carbalkoxy; and b is present as an additional bond.

12. A method of inhibiting growth of cells having hyperproliferative cell growth, comprising the step of exposing said cells to a growth inhibiting amount of a compound having the chemical formula:

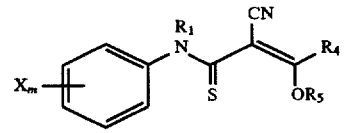

or a pharmaceutically acceptable salt thereof, wherein m is either 0, 1, 2, 3, 4 or 5;

each X is independently selected from the group consisting of halogen, trihalomethyl, and $NO_2$;

$R_1$ is hydrogen or unsubstituted lower alkyl;

$R_4$ is selected from the group consisting of unsubstituted lower alkyl, unsubstituted lower alkyl-optionally substituted aryl optionally containing up to five substituents each independently selected from the group consisting of unsubstituted lower alkoxy, halogen, trihalomethyl, SH, OH, NO₂, cyano, unsubstituted lower alkyl, unsubstituted lower alkenyl, unsubstituted lower alkynyl, amino, carboxy, and unsubstituted carbalkoxy, unsubstituted lower alkenyl-optionally substituted aryl optionally containing up to five substituents each independently selected from the group consisting of unsubstituted lower alkoxy, halogen, trihalomethyl, SH, OH, NO₂, cyano, unsubstituted lower alkyl, unsubstituted lower alkenyl, unsubstituted lower alkynyl, amino, carboxy, and unsubstituted carbalkoxy, and unsubstituted lower alkynyl-optionally substituted aryl optionally containing up to five substituents each independently selected from the group consisting of unsubstituted lower alkoxy, halogen, trihalomethyl, SH, OH, NO₂ cyano, unsubstituted lower alkyl, unsubstituted lower alkenyl, unsubstituted lower alkynyl, amino, carboxy, and unsubstituted carbalkoxy;

$R_5$ is selected from the group consisting of hydrogen, alkyl, C(=O)-unsubstituted lower alkyl, C(=O)-unsubstituted lower alkenyl, and C(=O)-unsubstituted lower alkynyl, and C(=O)-optionally substituted aryl optionally containing up to five substituents each independently selected from the group consisting of unsubstituted lower alkoxy, halogen, trihalomethyl, SH, OH, NO₂ cyano, unsubstituted lower alkyl, unsubstituted lower alkenyl, unsubstituted lower alkynyl, amino, carboxy, and unsubstituted carbalkoxy; and provided that $R_4$ and $R_5$ are not heterocyclic.

13. The method of claim 12, wherein $R_5$ is hydrogen.
14. The method of claim 12, wherein $R_1$ is hydrogen;

$R_4$ is methyl;

$R_5$ is hydrogen; and each X is independently selected from the group consisting of halogen and trihalomethyl.

15. A method of inhibiting growth of cells having hyper-proliferative cell growth, comprising the step of exposing said cells to a growth inhibiting amount of a compound having the chemical formula:

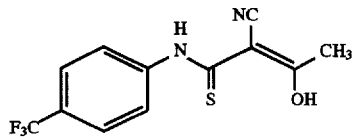

or a pharmaceutically acceptable salt thereof.

16. A method of treating a human patient suffering from a hyper-proliferative cell disorder comprising the step of administering to said patient a therapeutically effective amount of a compound having the chemical formula:

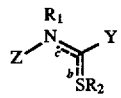

or a pharmaceutically acceptable salt thereof, wherein, $R_1$ is either hydrogen, alkyl, alkenyl, alkynyl, aryl, or is not present;

$R_2$ is either aryl, alkyl, alkenyl, alkynyl, or is not present;

Y is selected from the group consisting of aryl, alkyl, alkenyl, and alkynyl;

Z is selected from the group consisting of aryl, alkyl-aryl, alkenyl-aryl, and alkynyl-aryl;

b is an optional additional bond;

c is an optional additional bond;

provided that either b or c is present as an additional bond and if b is present as the additional bond $R_2$ is not present and c is not present, and if c is present as the additional bond $R_1$ is not present and b is not present; and provided that $R_1$, $R_2$, Y, and Z are not heterocyclic.

17. The method of claim 16, wherein $R_1$, if present, is selected from the group consisting of hydrogen, unsubstituted lower alkyl, unsubstituted lower alkenyl, unsubstituted lower alkynyl, and optionally substituted aryl optionally containing up to five substituents each independently selected from the group consisting of unsubstituted lower alkoxy, unsubstituted lower alkyl, unsubstituted lower alkenyl, unsubstituted lower alkynyl, halogen, trihalomethyl, SH, OH, NO₂, cyano, amino, carboxy, and unsubstituted carbalkoxy;

$R_2$, if present, is selected from the group consisting of unsubstituted lower alkyl, unsubstituted lower alkenyl, unsubstituted lower alkynyl, and optionally substituted aryl optionally containing up to five substituents each independently selected from the group consisting of unsubstituted lower alkoxy, unsubstituted lower alkyl, unsubstituted lower alkenyl, unsubstituted lower alkynyl, halogen, trihalomethyl, SH, OH, NO₂, cyano, amino, carboxy, and unsubstituted carbalkoxy;

Y is selected from the group consisting of:

lower alkyl optionally substituted with up to three substituents each independently selected from the group consisting of hydroxyl, cyano, unsubstituted lower alkoxy, =O, =S, NO₂, N(CH₃)₂, amino, and SH, lower alkenyl optionally substituted with up to three substituents each independently selected from the group consisting of hydroxyl, cyano, unsubstituted lower alkoxy, =O, =S, NO₂, N(CH₃)₂, amino, and SH, lower alkynyl optionally substituted with up to three substituents each independently selected from the group consisting of hydroxyl, cyano, unsubstituted lower alkoxy, =O, =S, NO₂, N(CH₃)₂, amino, and SH, and optionally substituted aryl optionally containing up to five substituents each independently selected from the group consisting of unsubstituted lower alkoxy, halogen, trihalomethyl, SH, OH, NO₂, cyano, unsubstituted lower alkyl, unsubstituted lower alkenyl, unsubstituted lower alkynyl, amino, carboxy, and unsubstituted carbalkoxy;

Z is selected from the group consisting of:

optionally substituted aryl optionally containing up to five substituents each independently selected from the group consisting of unsubstituted lower alkoxy, halogen, trihalomethyl, SH, OH, NO₂, cyano, unsubstituted lower alkyl, unsubstituted lower alkenyl, unsubstituted lower alkynyl, amino, carboxy, and unsubstituted carbalkoxy;

unsubstituted lower alkyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy;

unsubstituted lower alkenyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy; and unsubstituted lower alkynyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy.

18. The method of claim 17, wherein $R_1$ is hydrogen;

$R_2$ is not present;

Y is lower alkenyl optionally substituted with up to three substituents each independently selected from the group consisting of hydroxyl, cyano, unsubstituted lower alkoxy, =O, =S, $NO_2$, $N(CH_3)_2$, amino and SH;

Z is an optionally substituted phenyl optionally containing up to five substituents each independently selected from the group consisting of halogen, trihalomethyl, SH, OH, $NO_2$, cyano, unsubstituted lower alkoxy, unsubstituted lower alkyl, unsubstituted lower alkenyl, unsubstituted lower alkynyl, amino, carboxy, and unsubstituted carbalkoxy; and b is present as an additional bond.

19. A method of treating a human patient suffering from a hyper-proliferative cell disorder comprising the step of administering to said patient a therapeutically effective amount of a compound having the chemical formula:

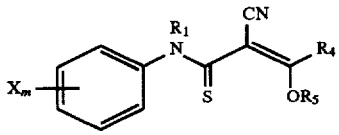

or a pharmaceutically acceptable salt thereof, wherein m is either 0, 1, 2, 3, 4 or 5;

each X is independently selected from the group consisting of halogen, trihalomethyl, and $NO_2$;

$R_1$ is hydrogen or unsubstituted lower alkyl;

$R_4$ is selected from the group consisting of unsubstituted lower alkyl, unsubstituted lower alkyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy, unsubstituted lower alkenyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy, and unsubstituted lower alkynyl-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy;

$R_5$ is selected from the group consisting of hydrogen, alkyl, C(=O)-unsubstituted lower alkyl, C(=O)-unsubstituted lower alkenyl, and C(=O)-unsubstituted lower alkynyl, and C(=O)-optionally substituted aryl optionally containing up to five substituents each independently selected from the group consisting of unsubstituted lower alkoxy, halogen, trihalomethyl, SH, OH, $NO_2$, cyano, unsubstituted lower alkyl, unsubstituted lower alkenyl, unsubstituted lower alkynyl, amino, carboxy, and unsubstituted carbalkoxy; and provided that $R_4$ and $R_5$ are not heterocyclic.

20. The method of claim 19, wherein $R_5$ is hydrogen.

21. The method of claim 19, wherein $R_1$ is hydrogen;

$R_4$ is methyl;

$R_5$ is hydrogen; and each X is independently selected from the group consisting of halogen and trihalomethyl.

22. The method of claim 19, wherein said disorder is a cancer selected from the group consisting of intra-axial brain cancer, ovarian cancer, colon cancer, prostate cancer, lung cancer, Kaposi's sarcoma, and melanoma.

23. The method of claim 22, wherein said cancer is glioma.

24. The method of claim 19, wherein said disorder is either a blood vessel proliferation disorder or a fibrotic disorder.

25. The method of claim 24, wherein said blood vessel proliferative disorder is either restenosis or atherosclerosis.

26. A method of treating a human patient suffering from a hyper-proliferative cell disorder comprising the step of administering to said patient a therapeutically effective amount of a compound having the chemical formula:

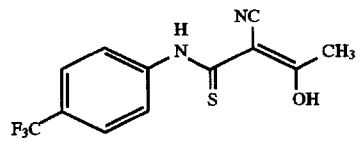

or a pharmaceutically acceptable salt thereof.

27. The method of claim 26, wherein said disorder is a cancer selected from the group consisting of intra-axial brain cancer, ovarian cancer, colon cancer, prostate cancer, lung cancer, Kaposi's sarcoma, and melanoma.

28. The method of claim 27, wherein said cancer is glioma.

29. The method of claim 26, wherein said disorder is either a blood vessel proliferation disorder or a fibrotic disorder.

30. The method of claim 29, wherein said blood vessel proliferative disorder is either restenosis or atherosclerosis.

* * * * *